United States Patent [19]

Calandruccio et al.

[11] Patent Number: 5,030,222

[45] Date of Patent: Jul. 9, 1991

[54] RADIOLUCENT ORTHOPEDIC CHUCK

[76] Inventors: James Calandruccio, 232 Patternson, Memphis, Tenn. 38111; James T. Canedy, 448 S. 82nd St., Omaha, Nebr. 68114

[21] Appl. No.: 521,273

[22] Filed: May 9, 1990

[51] Int. Cl.⁵ ............................................. A61F 5/04
[52] U.S. Cl. ..................................... 606/96; 606/97; 606/79; 606/80
[58] Field of Search .................. 606/96, 97, 98, 61, 606/64, 79, 80

[56] References Cited

U.S. PATENT DOCUMENTS

| | | | |
|---|---|---|---|
| 3,765,034 | 10/1973 | Johnston | 3/1 |
| 3,964,480 | 6/1976 | Froning | 606/61 |
| 4,541,424 | 9/1985 | Grosse et al. | 128/92 |
| 4,612,922 | 9/1986 | Barber | 606/80 X |
| 4,621,628 | 11/1986 | Brudermann | 128/92 VD |
| 4,625,718 | 12/1986 | Olerud et al. | 128/92 VD |
| 4,653,509 | 3/1987 | Olerud et al. | 128/749 |
| 4,667,664 | 5/1985 | Taylor | 606/64 |
| 4,686,997 | 8/1987 | Oloff et al. | 128/653 |
| 4,738,253 | 4/1988 | Buechel et al. | 128/92 VW |
| 4,738,254 | 4/1988 | Beuchel et al. | 128/92 VW |
| 4,788,970 | 12/1988 | Kara et al. | 128/92 ND |
| 4,803,976 | 2/1989 | Frigg et al. | 128/92 VD |
| 4,850,344 | 7/1989 | Olerud et al. | 606/97 |
| 4,881,535 | 11/1989 | Sohngen | 606/98 |
| 4,889,110 | 12/1989 | Galline et al. | 606/69 |
| 4,896,663 | 1/1990 | Vandewalls | 606/79 |
| 4,911,153 | 3/1990 | Border | 606/98 |

Primary Examiner—Robert A. Hafer
Assistant Examiner—Kerry Owens
Attorney, Agent, or Firm—John A. Beehner

[57] ABSTRACT

A radiolucent orthopedic chuck includes a housing having a driver stem protruding from the top surface and a drill bit protruding from the underside in radially spaced relation from the driver stem so as to displace a drill secured to the driver stem from the axis of the drill bit so that fluoroscopy may be used to ensure accurate alignment of the drill bit with a hole of an intramedullary nail both prior to and during its operation. A drive train interconnects the driver stem and drill bit for rotation in unison. All parts of the chuck but for the drill bit preferably radiolucent.

8 Claims, 8 Drawing Sheets

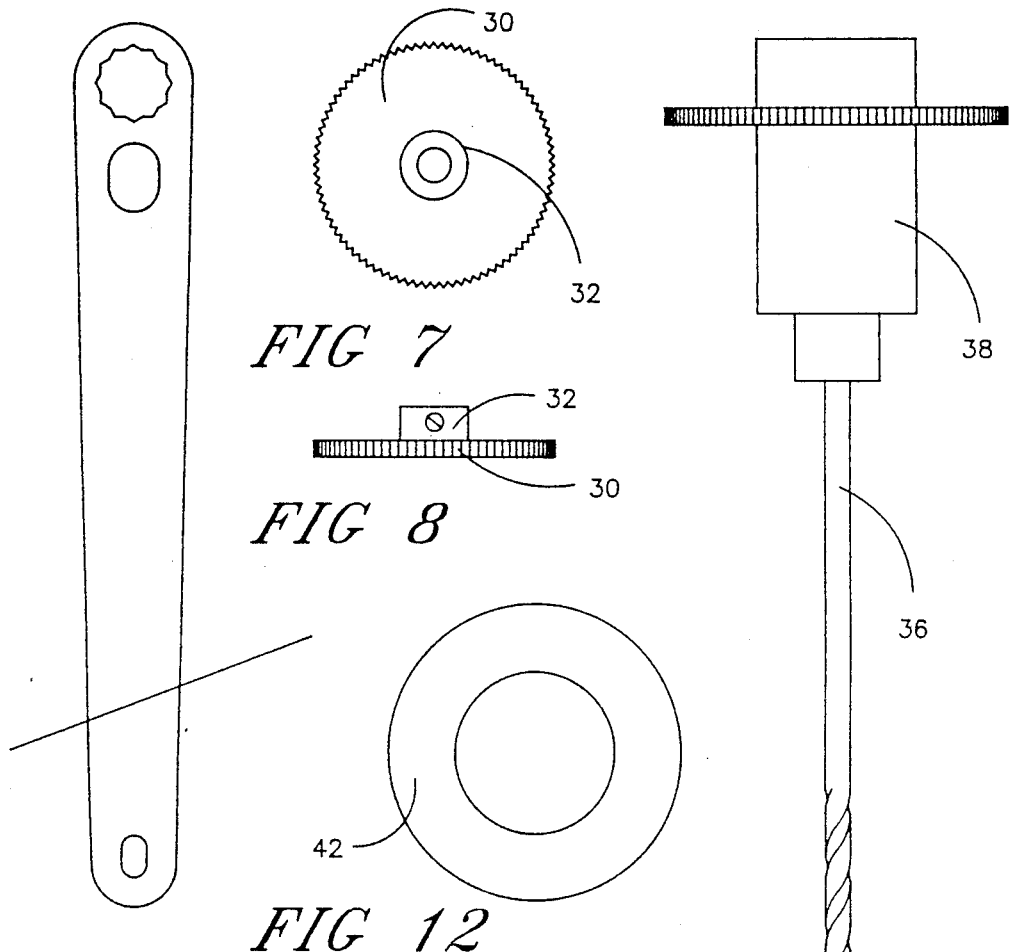

RADIOLUCENT ORTHOPEDIC CHUCK

BACKGROUND OF THE INVENTION

The present invention is directed generally to a radiolucent orthopedic drill chuck which displaces the drill bit sufficiently away from the orthopedic drill that x-rays may be directed axially of the bit without interference by the drill for prompt and precise alignment and drilling.

Although the critical applications for the present invention are diverse, its conception and prototypic clinical trials have involved intramedullary nails. In this country alone, annual tibia surgeries include approximately twenty-three thousand closed reductions and one hundred eleven thousand open reductions. Femur fractures result annually in approximately thirty-three thousand closed reductions and one hundred thirty-one thousand open reductions. For femur fractures, an elongated intramedullary nail is inserted through the center of the bone from an incision in the hip whereupon the nail is stabilized by a single screw inserted through the bone and nail at an angle to the axis of the nail. It has long been a problem to then accurately drill holes aligned with the holes at the distal end of the nail for the interlocking screws.

The current techniques include various free hand techniques as well as techniques using various stationary metal devices. Whereas a fluoroscope is used to assist with proper positioning of the drill, all of these techniques have in common the necessity for removing the fluoroscopic image while drilling. The problem inherent with all of these techniques therefore is that they in fact require blind drillings.

In one manual technique, a large incision is made near the distal end of the nail to expose the bone. The surgeon manipulates an awl to mark the drilling site on the bone with the aid of a fluoroscopic screen. The surgeon gets radiated while positioning the awl. The awl is then set by pounding it against the bone. Alternately, the holes may be drilled percutaneously by positioning the awl to mark the skin, after which the awl is removed and a drill is directed toward the bone through the marked spot on the skin. In either event, the double step of first marking the drilling location with an awl and then moving the awl and inserting a drill increases the chances for error over and above the inherent difficulty of blind drilling.

Certain of the positioning devices afford six degrees of freedom of movement but these require much education on the techniques of using the machine and still result in blind drilling.

Olerud, et al., U.S. Pat. No. 4,625,718 discloses an aiming apparatus for a wire drill. Whereas this devise enables live action sighting, it has several shortcomings which are believed to be resolved by the present invention. First, the Olerud apparatus is awkward for a surgeon to use since it has two handles on both sides of the fluoroscopic beam. Since the head of the x-ray machine is generally positioned about ten inches from the drilling site, it is awkward to reach in and manipulate both handles simultaneously. It requires the drill to be positioned at a right angle to its normal drilling position so that the drill is pushed sideways in an unfamiliar manner during use. Secondly, the metal around the opening of the Olerud, et al., device is radio opaque which is a big disadvantage for sighting. Finally, the Olerud device rotates a wire, not the actual drill bit. Since wire burns bone, it is not a good idea to drill bone with it. Furthermore, since the diameter of the wire is much smaller than a drill bit, it is very difficult to accurately center the wire within the larger diameter nail openings. If the wire opening is eccentrically positioned, a hollow drill bit following the wire will strike the nail rather than be directed through the distal hole as intended.

Accordingly, a primary object of the invention is to provide a radiolucent orthopedic drill chuck which displaces the drill bit from the radio opaque drill for live sighting of the drill bit during the operation.

Another object is to provide a radiolucent orthopedic chuck which protects the surgeon's hand from exposure to the fluoroscopic sighting beam.

Another object is to provide a radiolucent orthopedic chuck which is lightweight, simple in construction and readily usable without special instruction.

Another object is to provide a radiolucent orthopedic chuck which enables the drilling of a hole for an interlocking screw to be quickly and accurately performed thereby reducing trauma to the patient and x-ray exposure of the surgeon.

Another object is to provide a radiolucent orthopedic chuck which is substantially entirely radiolucent but for the drilling bit to afford optimum sighting in use.

Another object is to provide a radiolucent orthopedic chuck which is simple and rugged in construction, economical to manufacture and efficient in operation.

SUMMARY OF THE INVENTION

A radiolucent orthopedic chuck is provided for precision drilling of holes through which interlocking screws may be accurately directed through the distal holes of an intramedullary nail positioned within a bone. The chuck includes a housing having a rotatable upright driver stem accessible from the top of the housing for attachment to a power drill. A rotatable drill bit support device is positioned within the housing for supporting a drill bit in upright relation with the bit protruding from the underside of the housing at a position radially spaced from the driver stem. A power transfer mechanism on the driver stem and drill bit support device rotates the drill bit support device in response to rotation of the driver stem. Both the housing and drill bit support device are substantially radiolucent so that a fluoroscopic beam directed axially of a drill bit secured within the drill bit support device is effective both prior to and during the actual drilling operation for aligning the drill bit with one of the distal holes of an intramedullary nail. The drilling operation is thus substantially simplified by combining the aligning and drilling steps for reduced trauma to the patient and reduced exposure of the surgeon to x-rays.

The drill bit support device is a radially spaced from the driver stem sufficiently that a drill fixed on to the driver stem is displaced from the path of the fluoroscopic beam directed axially through a drill bit in the drill bit support device. Despite this displacement, it is preferred that the driver stem be oriented parallel to the drill bit so that the drill and chuck are advanced toward the bone by the same type of motion that is used by the surgeon without the chuck of the invention. The drill is stationarily secured relative to the chuck by a pair of universal brackets on the chuck. Likewise, whereas variances are easily built into the chuck, it is preferred that a drill bit supported within the chuck is rotated in the same direction as the driver stem and at the rotational speed so as to be most similar to that which the surgeon is already accustomed. It is furthermore preferred that the drill bit be permanently secured to a support collar within the housing and that the housing be formed of radiolucent plastic materials so that the entire chuck is disposable after each patient use for maintaining optimum sanitary conditions for the operation.

BRIEF DESCRIPTION OF THE DRAWINGS

FIG. 5 is an elevational view of the drill bit and support collar;

FIG. 6 is an elevational view of a drill attachment bracket;

FIG. 7 is a top plan view of the first gear for attachment to the driver stem;

FIG. 8 is a side elevational view of the first gear;

FIG. 9 is a top plan view of the idler gear;

FIG. 10 is a side elevational view of the idler gear;

FIG. 11 illustrates the housing securement screws;

FIG. 12 is a top plan view of a drill bit collar bearing;

FIG. 13 is a side sectional view of a drill bit collar bearing;

DESCRIPTION OF THE PREFERRED EMBODIMENT

Figure 1:
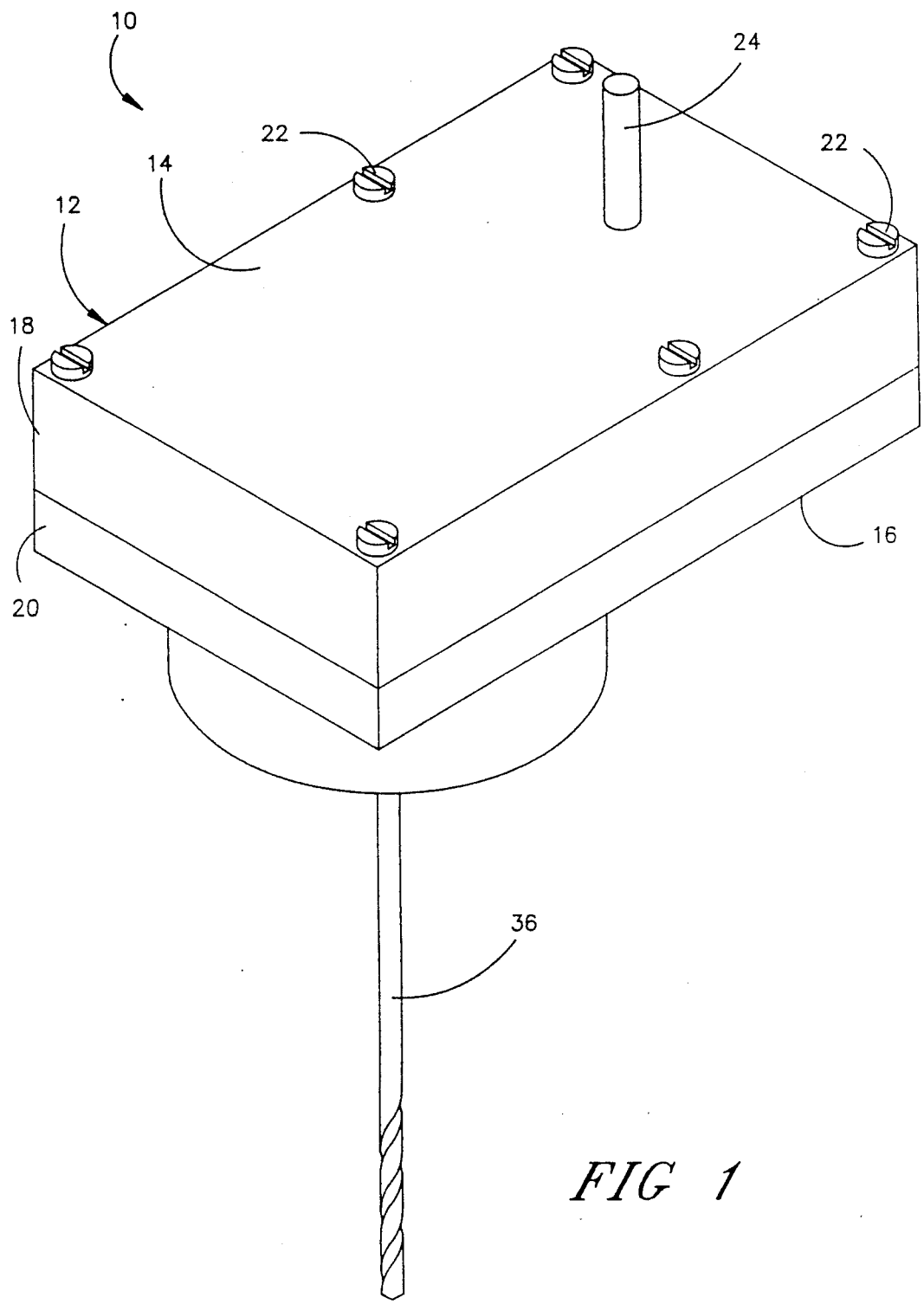
FIG. 1 is a perspective view of the radiolucent orthopedic chuck of the invention.
Figure 2:
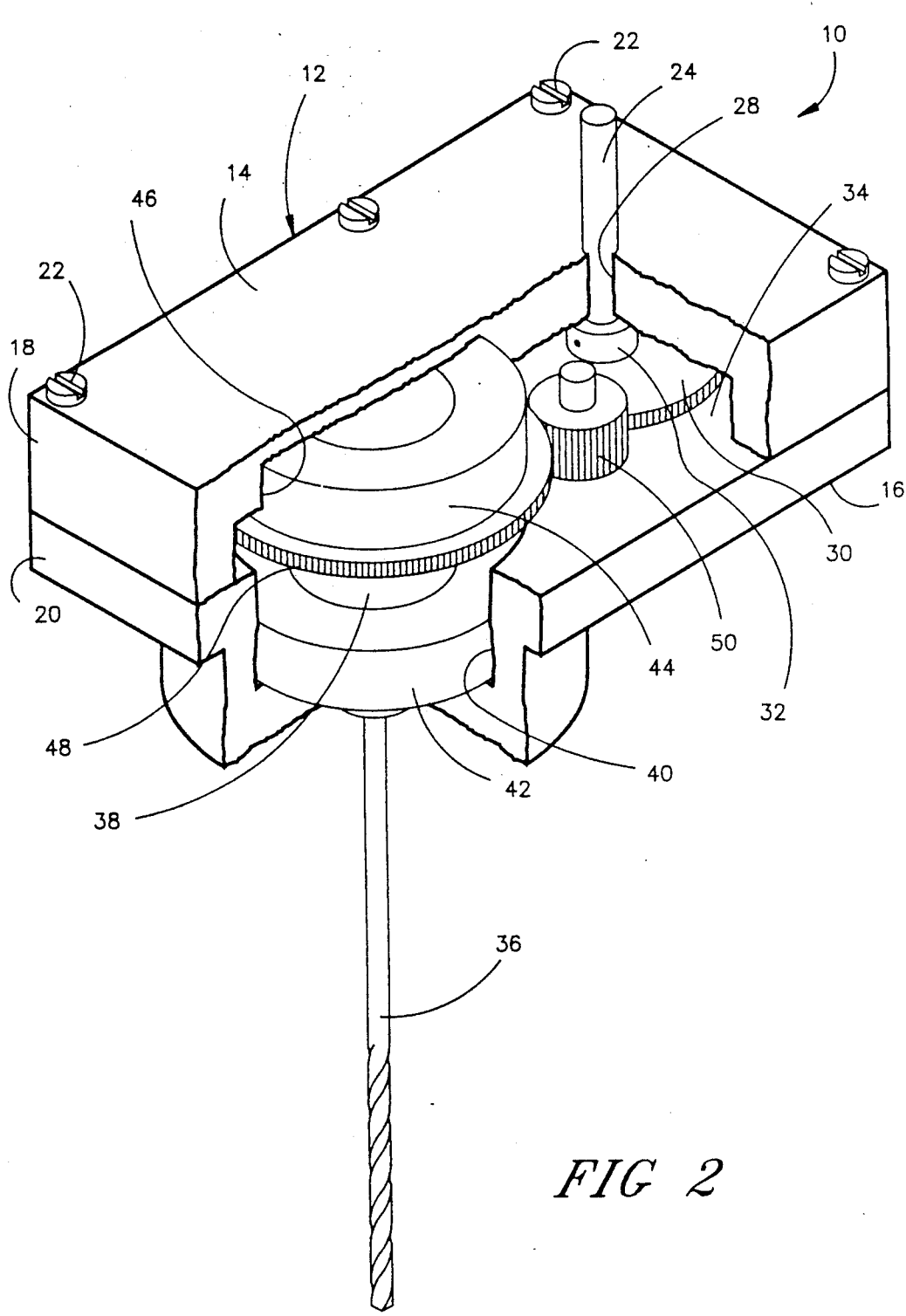
FIG. 2 is a perspective view of the invention with portions of the housing broken away for clarity.
Figure 3:
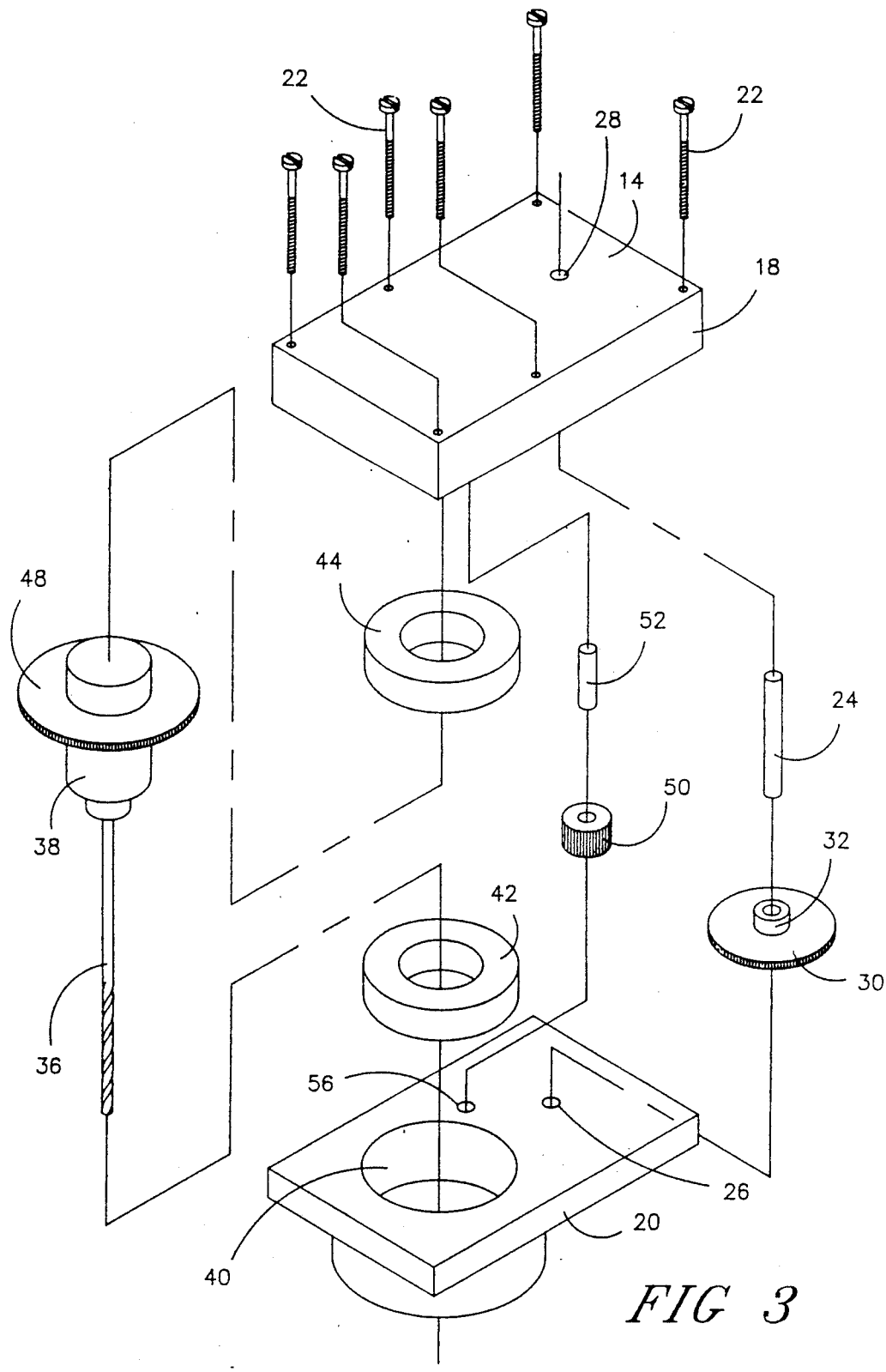
FIG. 3 is an exploded perspective view of the invention.
Figure 4:
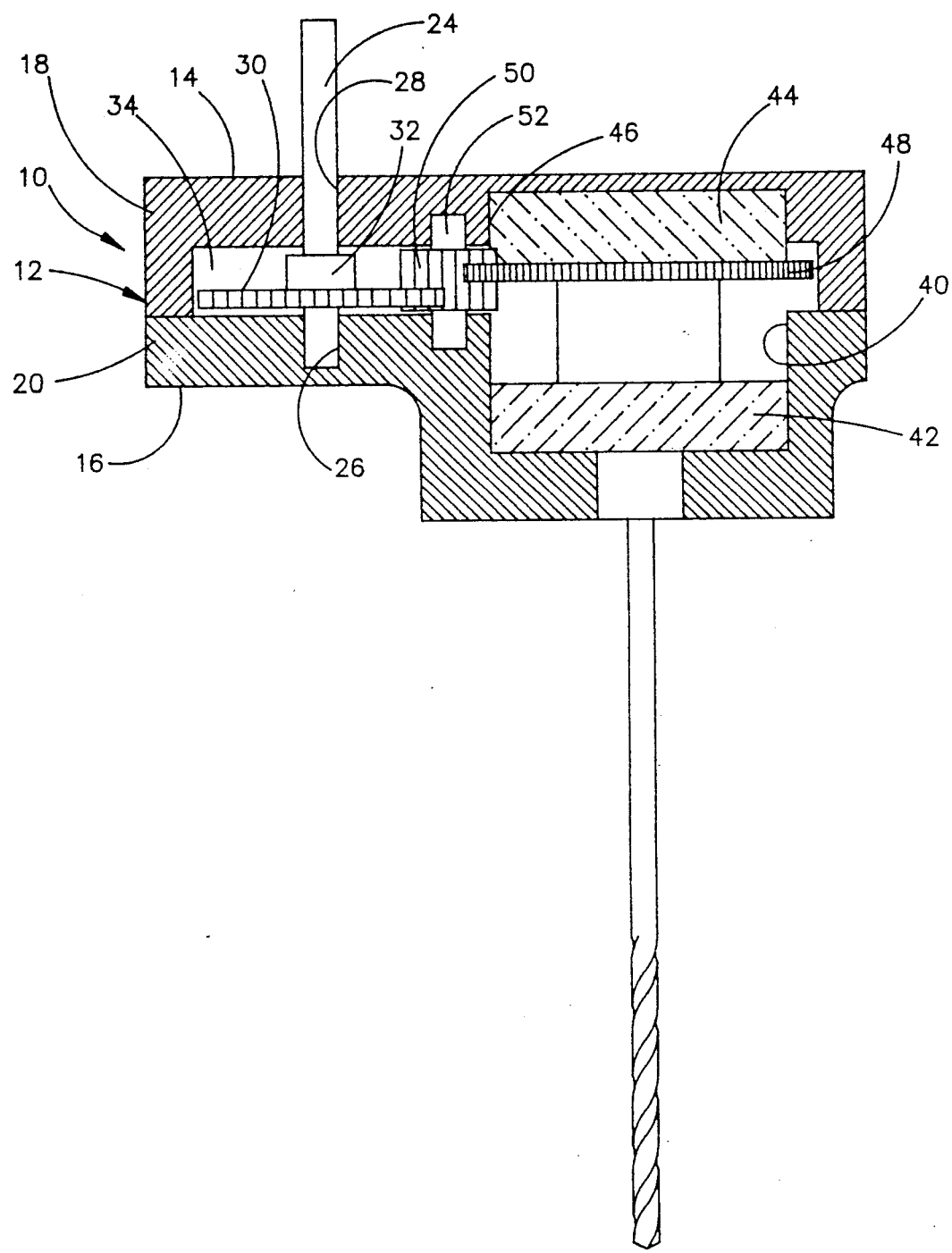
FIG. 4 is a rear partially sectional view of the invention.
Figure 14:
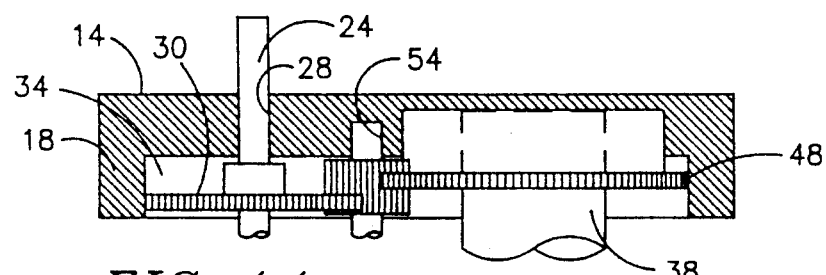
FIG. 14 is a partially sectional side view through the housing top half section.
Figure 15:
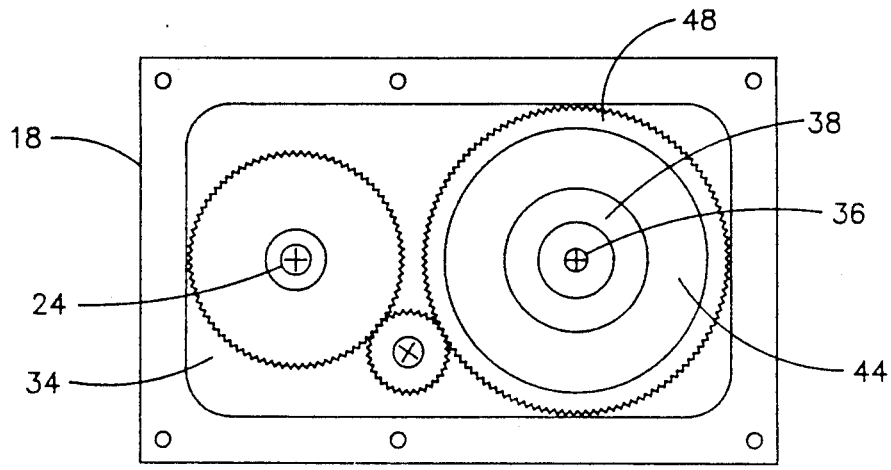
FIG. 15 is a bottom plan view of the housing top half section.
Figure 16:
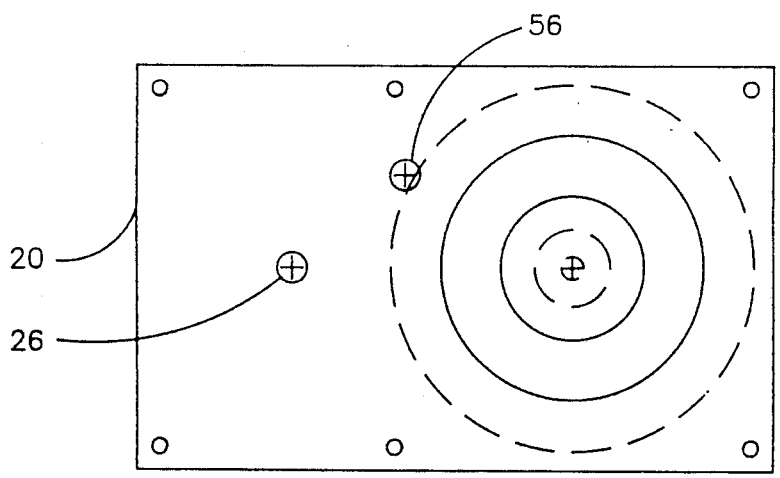
FIG. 16 is a top plan view of the housing bottom half section.
Figure 17:
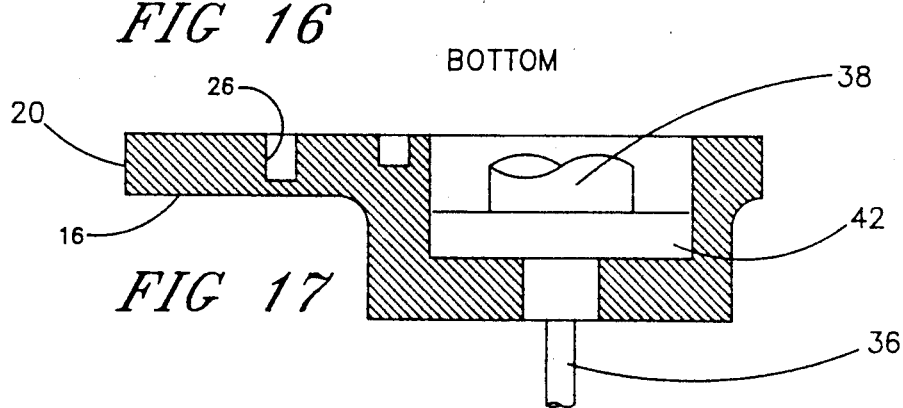
FIG. 17 is a partially sectional side view of the housing bottom half section.

The radiolucent orthopedic chuck 10 of the invention is shown in FIGS. 1, 2 and 3 including a housing 12 including a top surface 14 and underside 16. The housing is formed of top and bottom half sections 18 and 20 which are secured together by a plurality of screws 22. The shape of the housing and means for affording access to the internal components are not critical to the invention and may be designed as desired. For a disposable chuck, the housing half sections may be permanently secured together by adhesives or the like since access to the components within it would not be required for repair or cleaning.

An upright driver stem 24 seats within a recess 26 and protrudes upwardly through an opening 28 in housing top half section 18 for engagement by a surgeon's pneumatic drill in the same manner that the drill usually receives a drill bit. Stem 24 carries a first gear 30 and spacer 32 for rotation within housing chamber 34.

A drill bit 36 is received within a support collar 38 and is preferably permanently secured thereto for rotation in unison. For certain purposes, it may be desirable to manufacture a chuck with a replaceable drill bit but the sanitation advantages associated with a disposable chuck have been given precedence over that feature. Housing bottom half section 20 has a circular recess 40 formed therein for receiving a first bearing 42 into which the lower end of support collar 38 is received. A second bearing 44 fits over the upper end of support collar 38 and is received within a recess 46 in the housing top half section 18. The second bearing 44 rests on a second gear 48 which is permanently fixed onto the drill bit support collar 38 for rotation therewith.

Finally, a small idler gear 50 is carried on a stub shaft 52 receivable within aligned recesses 54 and 56 in the housing half sections at a position in meshed engagement with both the first and second gears 30 and 48. Accordingly, rotation of the driver stem 24 in a clockwise direction effects a counterclockwise rotation of idler gear 50 which produces a clockwise rotation of drill bit 36. It is preferred that the first and second gears 30 and 48 have an equal number of teeth so that the rotation of the drill bit is in a one to one relation with the rotation of the driver stem.

Referring to FIGS. 12 and 13, each of the first and second bearings includes an inner race 58, and outer race 60 and a plurality of balls engaged there between.

Figure 18:
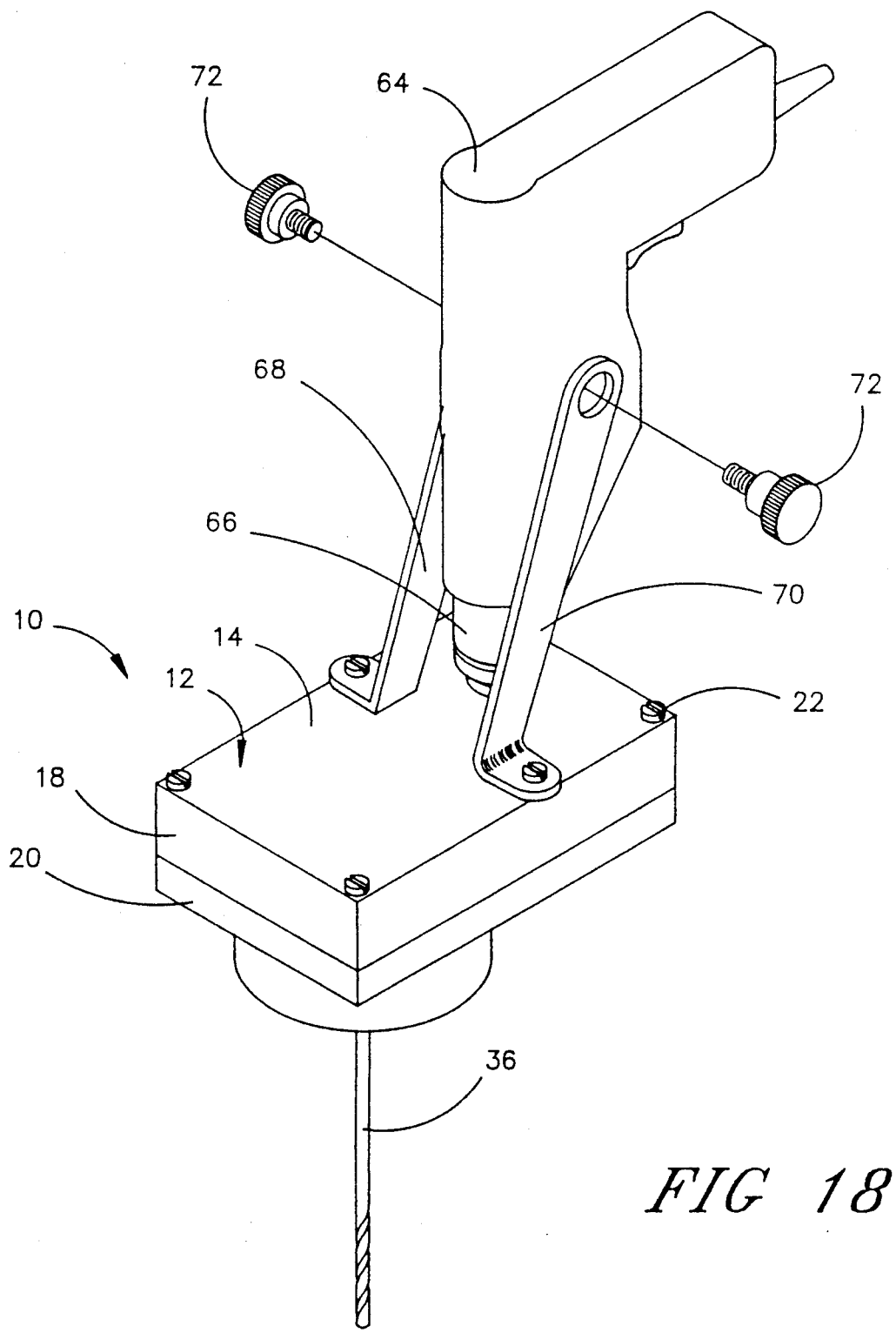
FIG. 18 is a perspective view of the radiolucent orthopedic chuck attached to an orthopedic drill.
Figure 19:
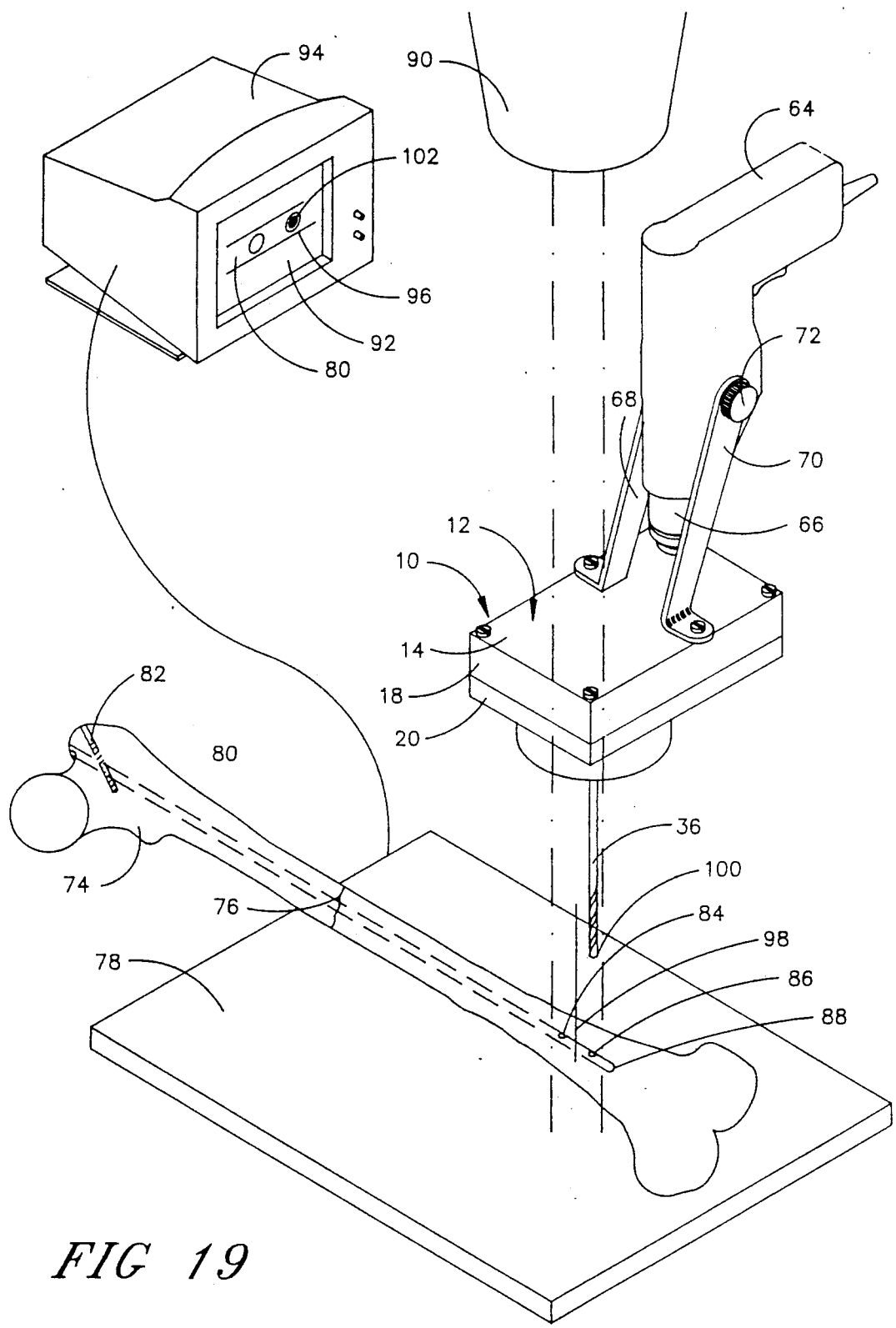
FIG. 19 is a perspective view of the invention in use for drilling of the femoral cortex during femoral intramedullary nailing.

The radiolucent orthopedic chuck 10 is adapted for connection to a conventional surgical drill 64 as illustrated in FIGS. 18 and 19. The conventional chuck 66 of drill 64 simply engages the driver stem 24 as illustrated. To secure housing 12 relative to the drill 64, a pair of brackets 68 and 70 are secured to housing top wall by a pair of the screws 22. The L-shaped brackets extend upwardly on opposite sides of the drill for detachable securement thereto by a pair of thumbscrews 72. Brackets may be designed to accommodate a drill of a particular manufacturer or a universal bracket may be provided for securement of any of the most common commercial surgical drills.

The operation of the radiolucent orthopedic chuck of the invention is described with reference to FIG. 19. In this illustration, a patient's femur 74 is fractured at 76. Whereas only the bone is illustrated, it is understood that that bone is incorporated within the leg of a patient whose leg is positioned to overlie a fluoroscopic receiver plate 78. After insertion of the intramedullary nail 80 in the usual manner and after securement of the nail by an inclined screw 82, the leg is positioned so that the pair of holes 84 and 86 adjacent the distal end 88 of the nail are positioned above and directed perpendicular to the receiver plate 78. An x-ray machine head 90 is positioned for directing a fluoroscopic beam downwardly through the leg so that the radio opaque nail 80 is visible on a fluoroscopic screen 92 of monitor 94.

All methods of drilling the interlocking screw holes begin with the obtainment of perfect circles on the fluoroscopic screen 92. This indicates that the axis of the fluoroscopic beam is parallel with the central axis 98 between the near and far screw holes 84 and 86 of the intramedullary nail 80.

Once this step is achieved, a skin cut is made and tip 100 of drill bit 36 is placed down on the near cortex of the bone and manipulated until the tip 100 is centered on the respective hole 86 on the fluoroscopic screen 92. The drill is then rotated upwardly until the axis of the bit 36 is collinear with the axis of the respective screw hole 86. This will be seen on the screen 92 as the prior perfect circle, representing hole 86, being converted to a thin ring of lucency 102. The thickness of the ring is the difference between the diameter of the screw hole 86 and the drill bit 36. Several still shots or live action, if so desired, may be taken during the drilling process to ensure accurate alignment of the drill bit with the nail holes 84 and 86. The drill is then depressed in the usual fashion to move the drill bit through the bone 74, the respective hole 86 of intramedullary nail 80 and into the bone on the opposite side of the nail. The drill and chuck are then withdrawn from the leg. During both the drilling and withdrawal, the drill is oriented in the usual position for drilling so as to be comfortably familiar to even a surgeon who has not previously used the chuck of the invention.

For optimum use of the chuck of the invention, it is preferred that the entire housing 12, drill bit support collar 38, first and second gears 30 and 48 and first and second bearings 42 and 44 all be formed of a radiolucent plastic material. Whereas the dimensions of one prototype chuck are five inches long by four inches wide by three inches deep, it is only important that the length of the chuck be sufficient to displace the drill 64 out of the path of x-rays directed through the drill bit 36.

The chuck of the invention may be used for both holes and any other drilling required for a single patient, after which the chuck is disposed of for reasons of sanitation. Whereas the drill bit may be formed of hard conventional metal material, the remaining parts may be formed of a radiolucent plastic material such as polyethylene. More expensive ultra-high molecular weight polymers could be used for nondisposable chucks having replaceable drill bits. Whereas a three sixteenths drill bit is most commonly used for fractures of the femur, a smaller bit is used for tibia fractures.

The radiolucent orthopedic chuck of the invention is a significant advantage for orthopedic surgery by combining in a single step the aligning and drilling functions, thereby significantly reducing the time of the operation resulting in both less trauma to the patient and less x-ray exposure to the surgeon.

Whereas the invention has been shown and described in connection with a preferred embodiment thereof, it is understood that many modifications, additions and substitutions may be made which are intended within the broad scope of the appended claims.

Thus there has been shown and described a radiolucent orthopedic chuck which accomplishes at least all of the stated objects.

We claim:

1. A radiolucent orthopedic chuck for precision live-action drilling of holes through which interlocking screws may be accurately directed through the holes of an intramedullary nail, said chuck comprising,
   a housing,
   an upright driver stem accessible from the top of said housing for attachment to a power drill,
   means for rotatably supporting a drill bit in upright relation with said bit protruding from the underside of said housing in radially spaced relation from said driver stem,
   coacting power transfer means on said driver stem and drill bit support means for rotating said drill bit support means in response to rotation of said driver stem,
   said housing and drill bit support means being substantially radiolucent whereby x-rays may be directed axially of a bit secured in said drill bit support means for aligning said bit with one of the holes of an intramedullary nail for precise drilling of holes into which interlocking nails are inserted,
   said drill bit support means being radially spaced from said driver stem sufficiently that an orthopedic drill engaging said driver stem is displaced from the path of x-rays directed axially through said drill bit,
   said drill bit support means comprising a collar having a central opening adapted to receive a drill bit therein for the rotation therewith, and
   said coacting power transfer means comprising a first gear secured to said driver stem within said housing, a second gear secured to said collar for rotation therewith, an idler gear in said housing and means for rotatably supporting said idler gear in meshed engagement with both of said first and second gears.

2. The radiolucent orthopedic chuck of claim 1 wherein said driver stem protrudes upwardly from the top of the housing.

3. The radiolucent orthopedic chuck of claim 1 wherein said coacting power transfer means is operative to rotate said drill bit support means in the same direction as said driver stem.

4. The radiolucent orthopedic chuck of claim 3 wherein said coacting power transfer means is operative to rotate the drill bit support means at the same speed of rotation as the driver stem.

5. The radiolucent orthopedic chuck of claim 1 wherein said drill bit support means further comprises upper and lower bearings fixed within said housing and adapted to engage said collar above and below said second gear respectively.

6. The radiolucent orthopedic chuck of claim 1 wherein said drill bit is fixed to said collar as a permanent part thereof.

7. The radiolucent orthopedic chuck of claim 1 wherein said housing comprises top and bottom half sections separable for access to the interior of the housing and means for securing said top and bottom half sections together.

8. The radiolucent orthopedic chuck of claim 5 wherein said housing, collar, gears and bearings are made of radiolucent plastic material.

* * * * *